United States Patent
Allmendinger et al.

(10) Patent No.: US 8,279,996 B2
(45) Date of Patent: Oct. 2, 2012

(54) BEAM HARDENING CORRECTION FOR CT PERFUSION MEASUREMENTS

(75) Inventors: Thomas Allmendinger, Forchheim (DE); Marc Kachelrieβ, Nürnberg (DE); Bernhard Schmidt, Fürth (DE); Philip Stenner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/914,226

(22) Filed: Oct. 28, 2010

(65) Prior Publication Data
US 2011/0103542 A1    May 5, 2011

(30) Foreign Application Priority Data
Oct. 30, 2009  (DE) .......................... 10 2009 051 384

(51) Int. Cl.
  *A61B 6/00*  (2006.01)
  *G06K 9/00*  (2006.01)
(52) U.S. Cl. .......................................... 378/4; 382/131
(58) Field of Classification Search .................. 378/4, 8, 378/207; 382/128
  See application file for complete search history.

(56) References Cited

U.S. PATENT DOCUMENTS

| | | | | |
|---|---|---|---|---|
| 5,953,444 | A * | 9/1999 | Joseph et al. ................. | 382/131 |
| 6,507,633 | B1 * | 1/2003 | Elbakri et al. .................... | 378/8 |
| 7,627,160 | B2 | 12/2009 | Avinash et al. | |
| 2003/0031299 | A1 * | 2/2003 | Ohishi .......................... | 378/162 |
| 2004/0252873 | A1 | 12/2004 | Avinash et al. | |
| 2006/0120507 | A1 * | 6/2006 | Brunner et al. ................. | 378/62 |
| 2008/0159469 | A1 * | 7/2008 | Ruhrnschopf et al. ........... | 378/4 |

FOREIGN PATENT DOCUMENTS
DE      102004028244 A1     12/2004

OTHER PUBLICATIONS

Improving PET/CT Attenuation Correction with Iterative CT Beam Hardening Correction M. Kaichelrielβ, and W.A. Kalender, IEEE Medical Imaging Conference REcord, vol. MO4-5 pp. 1905-1909; Magazine; 2005.
Assessment of perfusion by dynamic contrast-enhanced imaging using a deconvolution approach based on regression and singular value decomposition T.S. Koh, X.Y. Wu, L.H. Cheong and C.C. T. Lim, IEEE Transactions on Medical Imaging, vol. 23. pp. 1532-1542; Magazine; 2004.

(Continued)

*Primary Examiner* — Alexander H Taningco
(74) *Attorney, Agent, or Firm* — Harness, Dickey & Pierce, P.L.C.

(57) ABSTRACT

A method is disclosed for reconstructing image data of an examination subject from measured data, wherein a series of measured data sets has previously been acquired during a relative rotational movement between a radiation source of a computed tomography system and the examination subject and the measured data sets relate to the same section of the examination subject at succeeding instants in time. In at least one embodiment, first image data is reconstructed in each case from the measured data sets such that a series of first image data is available. A change variable indicating a change over time within the series of first image data is determined, and a distinction is made between different components of the examination subject in the first image data with the aid of the change variable. This distinction is used for beam hardening correction in an iterative algorithm for calculating enhanced image data.

18 Claims, 4 Drawing Sheets

OTHER PUBLICATIONS

Empirical cupping correction: A first order rawdataprocorrection for cone-beam computed tomography M. Kachelrieβ, K. Sourbelle and W. Kalender Med. Phys., vol. 33, No. 5, pp. 1269-1274; Magazine; 2006; DE.

Flash imaging in dual source CT (DSCT) H. Bruder, M. Petersilka, H. Mehldau, W. Heidinger, B.T. Schmidt, C. Thierfeld, K. Stierstorfer and T. Flohr E. Samei and J. Hsich, Eds., vol. 7258, No. 1, SPIE 2009, p. 7258D; Others; 2009; DE.

Computed tomography myocardial perfusion imaging: development points of emphaseis Expert Review of Cardiovascular Therapy, vol. 7. No. 2, pp. 99-101; Magazine; 2009; DE.

A comparative study of two postreconstruction beam hardening correction methods G. Herman and S. Trivedi, IEEE Transactions on Medical Imaging, vol. MI-2, No. 3, pp. 128-135; Magazine; 1983; DE.

Correction for beam hardening in CT G. Herman, Phys. Med. Biol., vol. 24, No. 1, pp. 81-106; Magazine; 1979; US.

A method for simultaneous correction of spectrum hardening artifacts in CT images containing both bone and iodine P.M Joseph and C. Ruth, Med Phys., vol. 24, No. 10, pp. 1629-1634; Magazine; 1997; US.

Correction for beam hardening in CT P. Kijewski and B. Bjarngard, Med. Phys., vol. 5, No. 3, pp. 209-214 May/Jun. 1978; Magazine; 1978; US.

Perfusion measurements of the brain; using dynamic CT for the quantitative assessment of cerebral ischemia in acute stroke E. Klotz and M. Koenig, European Radiology, vol. 30, pp. 170-184; Others; 1999; DE.

Theoretic basis and technical implementations of CT perfusion in acute ischemic stroke, part 2 Technical Implementations. American Journal of Neuroradiology, vol. 30, pp. 885-892,; Magazine; 2009.

Post-reconstructionmethod for beam hardening in CT, Phys. Med. Biol., vol. 24, No. 2, pp. 330-340; Magazine; 1979; US.

Perfusion CT: a worthwhile enhancement? The British Journal of Radiology, vol. 76, pp. 220-231; Magazine; 2003; GB.

A comparison of beam-hardening artifacts in x-ray CT with gadolinium and iodine contrast agents Med. Phys., vol. 22, No. 12, pp. 1977-1982; Magazine; 1995; US.

A simplified formulation of the gamma variate function M.T. Madsen, Phys. Med. Biol. vol. 37, No. 7, pp. 1597-1600: Magazine; 1992; US.

Beam hardening correction in CT myocardial perfusion measurement A. So, J. Hsieh, J.-Y. Li and T.-Y. Lee Phys. Med. Biol. vol. 54, pp. 3031-3050; Magazine; 2009; CA.

Contrast-enhanced first pass myocardial perfusion imaging: Correlation between myocardial blood flow in dogs at rest and during hyperemia N. Wilke, C. Simm, J. Zhang, J. Ellermann, X. Ya, H. Merkle, G. Path, H. Lüdermann, R.J. Bache and K. Ugurbil Magnetic REsonance in Medicine, vol. 29, pp. 485-497; Magazine; 1993.

Myocardial perfusion reserve: Assessment with multisection, quantitative, first-pass MR-imaging N. Wilke, M. Jerosch-Herold, Y. Wang, Y. Huang, B.V. Christensen, A.E. Stillman, K. Ugurbil, K. McDonald and R.F. Wilson, Radiology, vol. 204, pp. 373-384; Magazine; 1997; US.

Standardization of Computed Tomography Images by Means of a Material-Selective Beam Hardening Correction; P. Rüegsegger, Th. Hangartner, H.U. Keller, Th. Hinderling; Journal of Computer Assisted Tomography; vol. 2 pp. 184-188; Magazine; 1978; US.

First-Pass Nuclear Magnetic Resonance imaging Studies Using Gadolinium-DTPA in Patients With Coronary Artery Disease; Warren J. Manning, MD FACC, Dennis J. Atkinson, Ms. William Grossman, Sven Paulin, MD Robert R. Edelmann, Journal of te American College of Cardiology, vol. 18, pp. 959-965; Magazine; 1991; US.

Assessment of Myocardial Perfusion by Magnetic Resonance Imaging; J. Crnac, M.C. Schmidt, P. Theissen, U. Sechtem, Klinik III für Innere Medizin und Klinik und Poliklinik für Nukiearmedizin der Universtiät zu Köln, Herz vol. 22, No. 1, pp. 16-28; Magazine; 1997; DE.

German priority application DE 10 2009 051 384.1 filed on Oct. 30, 2009 and not yet published.

* cited by examiner

BEAM HARDENING CORRECTION FOR CT PERFUSION MEASUREMENTS

PRIORITY STATEMENT

The present application hereby claims priority under 35 U.S.C. §119 on German patent application number DE 10 2009 051 384.1 filed Oct. 30, 2009, the entire contents of which are hereby incorporated herein by reference.

FIELD

At least one embodiment of the invention generally relates to a method for reconstructing image data of an examination subject from measured data, wherein a series of measured data sets has previously been acquired during a relative rotational movement between a radiation source of a computed tomography system and the examination subject and the measured data sets relate to the same section of the examination subject at succeeding instants in time.

BACKGROUND

Methods for scanning an examination subject by way of a CT system are generally known. For example, typical methods employed in such cases are circular scans, sequential orbital scans with patient feed-through, or spiral scans. Other types of scan that are not based on circular movements are also possible, such as e.g. scans with linear segments. Absorption data of the examination subject is acquired from different recording angles with the aid of at least one X-ray source and at least one oppositely located detector, and the thus collected absorption data or, as the case may be, projections are computed by means of appropriate reconstruction methods into sectional images (slices) through the examination subject.

In order to reconstruct computed tomographic images from X-ray CT data sets of a computed tomography device (CT scanner), i.e. from the acquired projections, a method referred to as filtered back-projection (FBP) is currently employed as the standard procedure. Following the data acquisition a so-called "rebinning" step is performed in which the data generated by means of the beam spreading out from the source in the shape of a fan is reordered in such a way that it is available in a form as though the detector had been impinged upon by X-ray beams converging in parallel onto the detector. The data is then transformed into the frequency domain. Filtering takes place in the frequency domain and subsequently the filtered data is back-transformed. A back-projection onto the individual voxels within the volume of interest is then performed with the aid of the thus re-sorted and filtered data.

Iterative reconstruction methods have recently been developed wherein initial image data is first reconstructed from the projection measured data. A convolution back-projection method, for example, can be used for this purpose. Synthetic projection data is then generated from said initial image data by means of a "projector", that is to say a projection operator which is intended to mathematically map the measurement system as accurately as possible. The difference with respect to the measurement signals is then back-projected using the adjoint operator associated with the projector and in this way a residuum image is reconstructed and used to update the initial image. The updated image data can in turn be used in order to generate new synthetic projection data in a next iteration step with the aid of the projection operator, the difference with respect to the measurement signals can once again be formed therefrom, and a new residuum image can be computed and in turn used to enhance the image data of the current iteration step, etc. By way of such a method it is possible to reconstruct image data that provides relatively good image definition and nonetheless exhibits low image noise.

Different types of artifacts can appear in the CT images depending on conditions during the measured data acquisition and depending on the examination subject being studied in a particular case. Beam hardening artifacts are an example of this. These are produced due to the fact that the radiation emitted by the CT X-ray source is not monochromatic, but polychromatic, and that the attenuation of the X-ray radiation is dependent on its energy in a particular instance. Furthermore, different materials have different energy-dependent attenuation profiles. Artifacts are produced if this is not taken into account during the image reconstruction. This is particularly serious if components of the examination subject having high attenuation values are present.

SUMMARY

In at least one embodiment of the invention, a method is disclosed for reconstructing CT images wherein it is aimed to avoid beam hardening artifacts. Further, a corresponding control and computing unit, a CT system, a computer program, and a computer program product are disclosed.

Advantageous embodiments and developments are the subject matter of dependent claims.

With at least one embodiment of the inventive method for reconstructing image data of an examination subject from measured data, a series of measured data sets is first acquired in the course of a relative rotational movement between a radiation source of a computed tomography system and the examination subject; in this case the measured data sets relate to the same section of the examination subject at succeeding instants in time. First image data is reconstructed in each case from the measured data sets, with the result that a series of first image data is available. A change variable is determined which indicates a change over time within the series of first image data. With the aid of the change variable a distinction is made between different components of the examination subject in the first image data. This distinction is used for beam hardening correction in an iterative algorithm for calculating enhanced image data.

There is therefore measured data available not just for an individual image that is to be reconstructed, but for a series of images. These represent a sequence of images over time. Since the measured data contains the same section of the examination subject it is accordingly possible to derive from the image series how said section has changed over time in the course of the measurements. A procedure of said kind is suitable in particular for perfusion measurements.

Following the first image reconstruction a first image is available for each measured data set. Due to the beam hardening, however, these first images are artifact-laden. This undesired effect is reduced by means of the subsequent procedure. For this purpose a change variable is first determined. From said variable it is possible to derive information concerning whether changes exist between the various first images and/or how great said changes are. Since the series of first images represents a time sequence, the change variable therefore indicates a change over time within the section of the examination subject that is under investigation.

The change variable is used to distinguish between different components of the examination subject. This discrimination is possible because there can be components which remain constant over time in terms of their behavior, and other components which change with time.

An iterative algorithm is used in order to enhance the image data by reducing the artifacts produced due to the beam hardening. Said iterative algorithm preferably starts with the first image data. The iterative algorithm is in this case constructed in such a way that it accomplishes a beam hardening correction. The determined discrimination between the different components is incorporated into said correction.

In a development of at least one embodiment of the invention the change variable specifies a change value pixel by pixel for the series of first image data. For each pixel there are therefore one or more values available from which information about the change over time can be derived.

It is particularly advantageous if, for the purpose of differentiating between different components using the change variable, a distinction is made between static and dynamic components. This is possible owing to the temporal information that is provided by the change variable. Static components are components which, over the series of first images, have not changed or have changed little in terms of their arrangement in the image. Dynamic components, in contrast, have moved in the course of the series of images, e.g. by appearing, disappearing, or changing in size or shape.

It is also particularly advantageous if, for the purpose of differentiating between different components within the static components using the first image data, a distinction is made between components attenuating X-ray beams to different degrees. In this way image regions having static and strongly attenuating materials, and image regions having static and only slightly attenuating materials can therefore be specified and separated from one another. This differentiation is made possible through consideration of the values of the first image data. Equally it is advantageous if, for the purpose of differentiating between different components within the dynamic components using the first image data, a distinction is made between components attenuating x-ray beams to different degrees. In this way image regions having dynamic and strongly attenuating materials, and image regions having dynamic and only weakly attenuating materials can therefore be specified and separated from one another. This differentiation too is made possible through consideration of the values of the first image data.

In an embodiment of the invention a distinction is made between the components water, bone and contrast agent. The contrast agent can be in particular iodine, which is routinely employed in perfusion measurements. These three components are significantly different from one another in terms of their energy dependence of the attenuation of X-ray radiation, so a separation thereof in the case of a beam hardening correction is of particular interest.

According to a development of at least one embodiment of the invention a plurality of part-image data corresponding to the different components is determined from the first image data. This means that for each component there is in each case a part-image present from which it can be derived at which pixels the respective component is located.

It is furthermore advantageous in connection with the part-image data if when the iterative algorithm is executed the first image data is subjected to a forward projection in which the part-image data is linked with an X-ray-energy-dependent attenuation variable that is specific to the respective component. This allows a very precise beam hardening correction.

According to a development of at least one embodiment of the invention the change variable is corrected prior to the distinction being made between different components by at least partially removing movements of the examination subject from the change variable. Preferably a gradient formation is used for this purpose within the individual first images. If the movements of the examination subject, such as e.g. cardiac movement, respiratory movement, change in position, are factored out of the change variable, said thus corrected change variable can be used to distinguish the components from one another more effectively.

The control and computing unit according to at least one embodiment of the invention serves for reconstructing image data of an examination subject from measured data acquired by a CT system. The unit includes a program memory for storing program code, there being resident herein—possibly inter alia—program code that is suitable for performing a method of the above-described type. The CT system according to at least one embodiment of the invention includes such a control and computing unit. In addition it can include other component parts that are required e.g. for the purpose of acquiring measured data.

The computer program according to at least one embodiment of the invention possesses program code segments that are suitable for performing at least one embodiment of the method of the above-described type when the computer program is executed on a computer.

The computer program product according to at least one embodiment of the invention comprises program code segments stored on a non-transitory computer-readable data medium that are suitable for performing a method of the above-described type when the computer program is executed on a computer.

BRIEF DESCRIPTION OF THE DRAWINGS

The invention is explained in more detail below with reference to an example embodiment and the attached drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
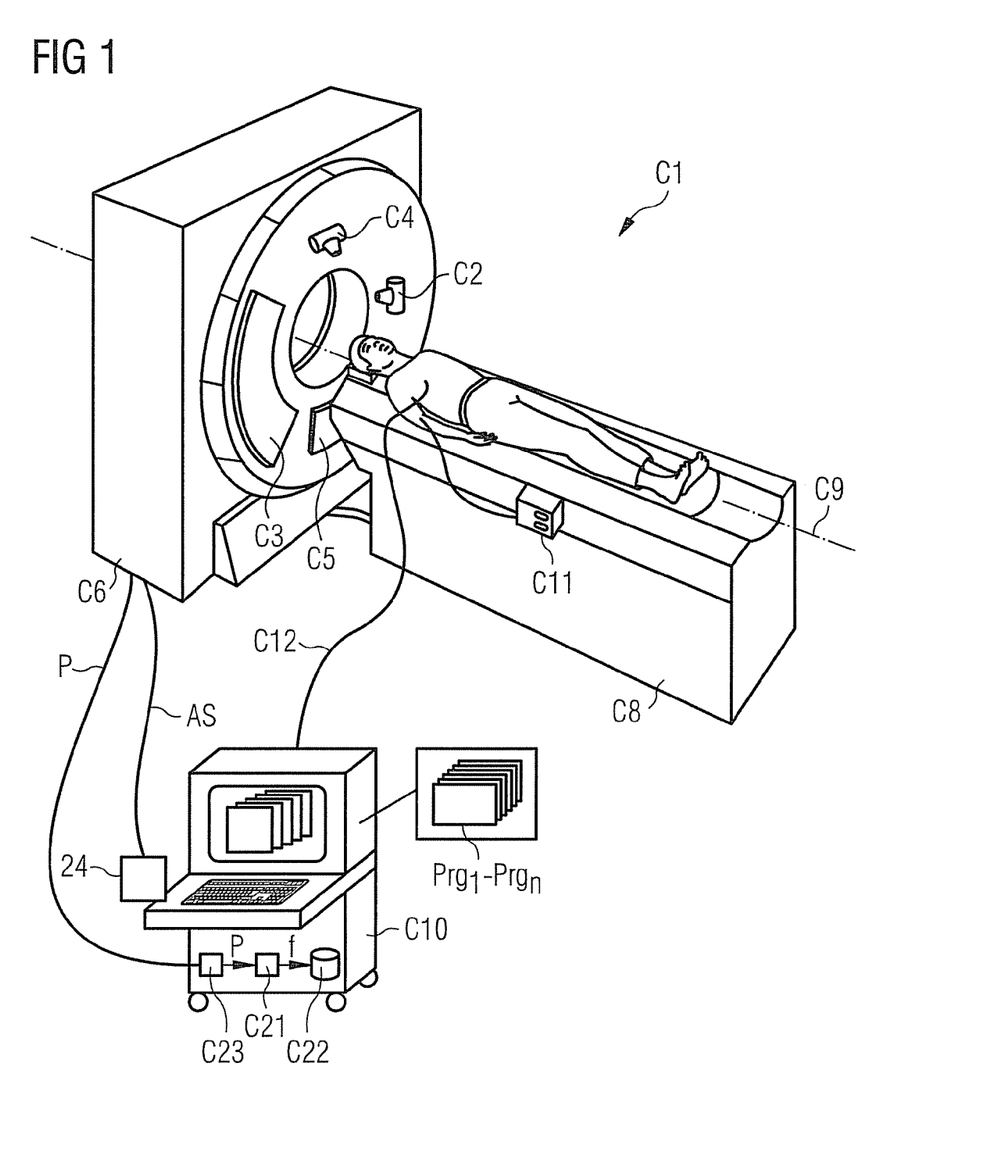
FIG. 1: shows a first schematic representation of an example embodiment of a computed tomography system having an image reconstruction component.

FIG. 1 firstly shows a schematic representation of a first computed tomography system C1 having an image reconstruction device C21. Located in the gantry housing C6 is a closed gantry (not shown here) on which is disposed a first X-ray tube C2 having an oppositely located detector C3. Optionally there is disposed in the CT system shown here a second X-ray tube C4 having an oppositely located detector C5, such that a higher time resolution can be achieved by virtue of the additionally available emitter/detector combination; alternatively, if different X-ray energy spectra are used in the emitter/detector systems, "dual energy" examinations can also be performed.

The CT system C1 also includes a patient couch C8 on which a patient can be moved along a system axis C9, also referred to as the z-axis, during the examination into the measurement field, with the scanning itself being able to take place both as a pure circular scan without patient feedthrough exclusively in the examination region of interest. In this arrangement the X-ray source C2 or, as the case may be, C4 rotates around the patient in each case. In parallel the detector C3 or, as the case may be, C5 co-rotates opposite the X-ray source C2 or, as the case may be, C4 in order to acquire projection measured data which is then used for reconstructing slices. Alternatively to a sequential scan, in which the patient is moved incrementally through the examination field between the individual scans, it is, of course, also possible to perform a spiral scan, in which the patient is moved continuously along the system axis C9 through the examination field between X-ray tube C2 or, as the case may be, C4 and detector C3 or, as the case may be, C5 during the revolving scanning with the X-ray radiation. In a spiral scan the movement of the patient along the axis C9 and the simultaneous rotation of the X-ray source C2 or, as the case may be, C4 results in the X-ray source C2 or, as the case may be, C4 following a helical path relative to the patient during the measurement. This path can also be realized by moving the gantry along the axis C9 while the patient remains motionless.

The CT system 10 is controlled by way of a control and computing unit C10 having computer program code $Prg_1$ to $Prg_n$ residing in a memory. It is pointed out that said computer program codes $Prg_1$ to $Prg_n$ can, of course, also be contained on an external storage medium and be loaded into the control and computing unit C10 as required. Acquisition control signals AS can be transmitted from the control and computing unit C10 via a control interface 24 for the purpose of controlling the CT system C1 in accordance with specific measurement protocols.

The projection measured data p (also referred to below as raw data) acquired by the detector C3 or, as the case may be, C5 is passed via a raw data interface C23 to the control and computing unit C10. Following suitable preprocessing where necessary, said raw data p is then processed further in an image reconstruction component C21. In this exemplary embodiment the image reconstruction component C21 is implemented in the control and computing unit C10 in the form of software on a processor, e.g. in the form of one or more of the computer program codes $Prg_1$ to $Prg_n$. With regard to the image reconstruction the same applies as already explained in relation to the control of the measurement process, namely that the computer program codes $Prg_1$ to $Prg_n$ can also be contained on an external storage medium and be loaded as required into the control and computing unit C10.

The image data f reconstructed by the image reconstruction component C21 is then stored in a memory C22 of the control and computing unit C10 and/or output in the usual way on the screen of the control and computing unit C10. The data can also be fed via an interface that is not shown in FIG. 1 into a network connected to the computed tomography system C1, a radiological information system (RIS) for example, and stored in a mass storage that is accessible there or can be output as images.

In addition, the control and computing unit C10 can also perform the function of an ECG, a lead C12 being used to transmit the ECG potentials between patient and control and computing unit C10. In addition the CT system C1 shown in FIG. 1 also includes a contrast agent injector C11 via which contrast agent can additionally be injected into the patient's bloodstream so that the patient's vessels, in particular the ventricles of the beating heart, can be visualized more clearly. Furthermore there is also the possibility herewith to perform perfusion measurements, for which the proposed method is particularly suitable.

Figure 2:
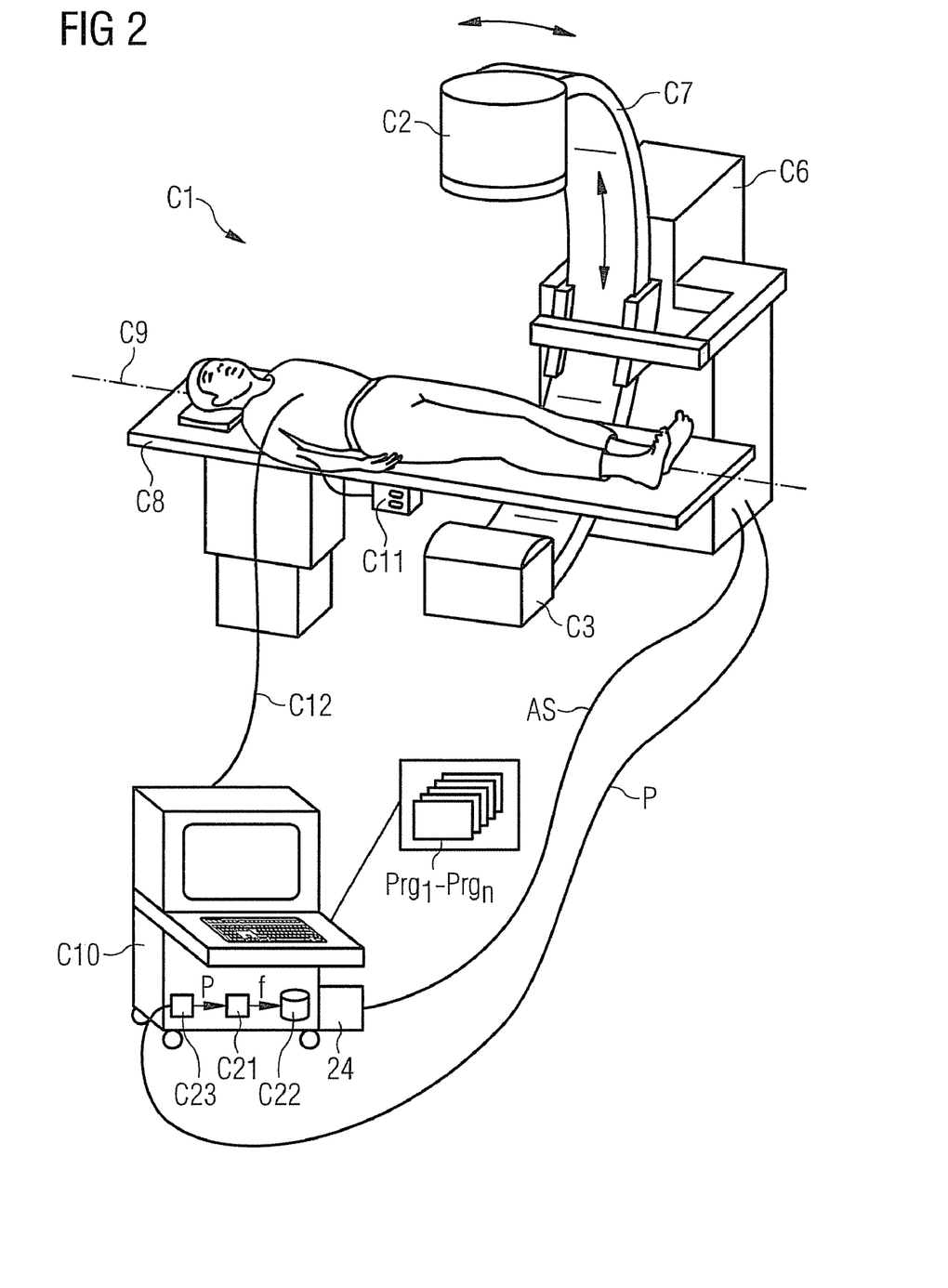
FIG. 2: shows a second schematic representation of an example embodiment of a computed tomography system having an image reconstruction component.

FIG. 2 shows a C-arm system in which, in contrast to the CT system shown in FIG. 1, the housing C6 carries the C-arm C7 to which the X-ray tube C2 is secured on one side and the oppositely located detector C3 on the other. In order to perform a scan, the C-arm C7 is likewise pivoted around a system axis C9, such that scanning can take place from a plurality of scanning angles and corresponding projection data p can be determined from a plurality of projection angles. The C-arm system C1 shown in FIG. 2, like the CT system from FIG. 1, has a control and computing unit C10 of the type described with reference to FIG. 1.

At least one embodiment of the invention can be applied in both of the systems shown in FIGS. 1 and 2. Furthermore it can also be used in principle for other CT systems, e.g. for CT systems having a detector forming a complete ring.

In perfusion measurements a contrast agent is administered into the bloodstream of the examination subject and then a plurality of CT scans are taken sequentially in time. There is therefore a series of CT images available, enabling the variation with time of the contrast agent contained in the blood and transported with it to be seen in the examination subject. From this temporal information about the blood flow volume it is possible to identify defects, thus e.g. due to a delay in the arrival of the contrast agent at a specific point. Ischemic regions of the heart, i.e. sites in the cardiac muscle experiencing circulatory malfunctions, are of particular interest. These can point to an impending myocardial infarction. CT techniques of this kind relating to the cardiac muscle are referred to as CT myocardial perfusion assessments.

Iodine is normally used as a contrast agent. This is highly absorbent for X-ray radiation, so it is very visible in the CT image. The CT values of iodine lie between 300 and 500 HU (Hounsfield Units). These high values are typically reached in the blood vessels or heart ventricles, in which the iodine still has a high concentration; in the muscle the value is smaller, usually in the order of approx. 100 HU. Accordingly the concentration of iodine in the muscle is easily identifiable, even in diluted form, with the aid of the CT images.

Polychromatic X-ray radiation is used in CT. When X-ray radiation passes through matter the low-energy component of the X-ray beams is attenuated more strongly, i.e. absorbed and scattered, than the high-energy component. Polyenergetic radiation is therefore hardened during its passage through matter. This effect makes itself particularly noticeable when highly absorbing materials, such as e.g. bone or iodine, are situated close to one another. The CT values of the soft tissue lying therebetween are greatly underestimated in this case. These artifacts correspond to the so-called cupping effect. They are referred to as beam hardening artifacts.

In the evaluation of perfusion measurements, e.g. in cardiac CT, a constant layer position is repeatedly scanned over a time period of typically 30 seconds. The previously administered contrast agent perfuses the myocardium and time-density curves are obtained which allow a perfusion analysis of the scanned tissue. In this process highly accurate CT values are essential, since the results obtained in relation to the blood flow will otherwise be unreliable. Beam hardening artifacts therefore constitute a particular problem in perfusion measurements. In particular at the time instants at which the contrast agent bolus flows through the ventricle and/or the aorta, interfering beam hardening artifacts are produced which make a correct determination of the perfusion impossible. This is due to the high attenuation value of the contrast agent. Efforts are therefore directed at reducing the beam hardening artifacts as far as possible by suitable measures.

There exists a multiplicity of simple methods for beam hardening correction. These normally include a water precorrection. In this case it is assumed that the tissue being examined has an energy-dependent attenuation corresponding to that of water. All the CT values are therein normalized to those of water. Examples of methods of this kind are described in the following documents, the entire contents of each of which are hereby incorporated herein by reference:

P. Kijewski, B. Bjarngard: Correction for beam hardening in CT, Med. Phys. Vol. 5, no. 3, pp. 209-214, May/June 1978;

G. Hermann: Correction for beam hardening in CT, Phys. Med. Biol., vol. 24, no. 1, pp. 81-106, 1979; and M. Kachelrieβ, K. Sourbelle, W. Kalender: Empirical Cupping Correction: a first order raw data precorrection for cone beam computed tomography, Med. Phys., vol. 33, no. 5, pp. 1269-1274, May 2006.

Since the values are normalized to the energy dependence of water, errors arise for all other materials. These standard precorrections break down accordingly in particular when materials with a higher atomic number such as e.g. bone or iodine are present in the image. In this case the above-described beam hardening artifacts are produced in spite of the precorrection. It is therefore advantageous to perform an iterative image reconstruction in which beam hardening artifacts are reduced from iteration to iteration. The basis of the iterative method consists in taking into account the correct energy dependence of different components of the examination subject in the forward projection, since the energy dependencies are known, though not the spatial distribution of the respective materials in the image.

Figure 3:
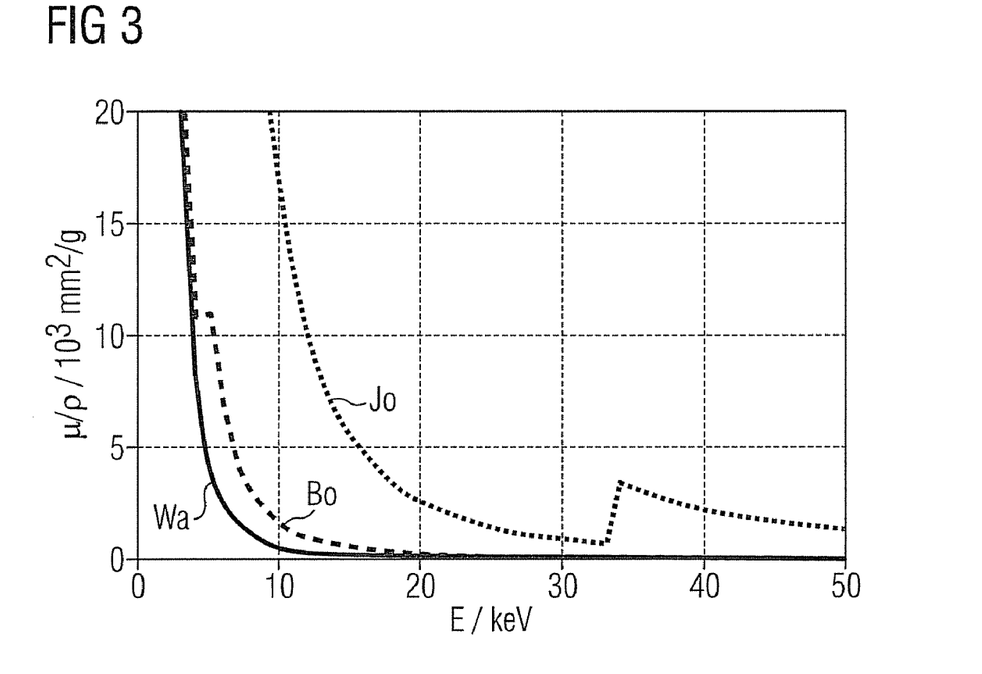
FIG. 3: shows an energy-dependent attenuation profile for three different materials.

FIG. 3 shows the X-ray radiation attenuation per density $\mu/\rho$ in $$10^3 \frac{mm^2}{g}$$

of the material for three different materials as a function of the energy of the X-ray radiation E in keV. The graph shows the curve for water Wa, the curve for bone Bo, and the curve for iodine Jo. It can be clearly seen that although bone and iodine both have high CT attenuation values, they are different from each other in terms of the energy dependence of the attenuation. This applies in particular to the K-edge of iodine at 35 KeV, at which the attenuation of bone is very low. It is therefore disadvantageous to focus solely on bone in the beam hardening correction, without differentiating this component from iodine. For in this way beam hardening artifacts produced due to the presence of iodine will not be removed.

In the following it is first explained how the update equation or, as the case may be, iteration equation used for the iterative algorithm is obtained. The measured data is acquired first. As is customary with perfusion measurements, the data is acquired at a plurality of time instants such that a series of measured data is available. A first image f is calculated from said data by means of a reconstruction algorithm $R_f^{-1}$ in each case. The index f of the reconstruction algorithm $R_f^{-1}$ indicates therein that a water precorrection is applied which leads to beam hardening artifacts for all materials whose energy-dependent attenuation is significantly different from water.

A series of first images f is now available. Due to the beam hardening these are laden with artifacts. The desired result image that is free of beam hardening artifacts is designated by g. A polychromatic Radon transform operator $R_g$ is sought such that the following applies:

$$R_f f = R_g g \qquad \text{Formula (1)}$$

The expression $R_f f$ on the left side of the equation is the measured data; this is obtained by applying the forward projection $R_f$ to the first image f.

The Radon transform operator $R_g$ is intended to be polychromatic to the extent that it takes into account not only the energy dependence of the attenuation of water, but also of different materials.

In order to obtain the iteration equation, formula (1) is rewritten using $R_g = R_g + R - R$. In this case R is a monoenergetic Radon transform, i.e. a simple line integral along the beam L: $Rf = \int dL f$. R is invertible.

Through insertion in formula (1) one arrives at:

$$R_f f = (R_g + R - R) g \qquad \text{Formula (2)}$$

After application of $R^{-1}$ on both sides this leads to:

$$g = g + R^{-1}(R_f f - R_g g) \qquad \text{Formula (3)}$$

The update or iteration equation follows directly herefrom:

$$g^{(n+1)} = g^{(n)} + R^{-1}(R_f f - R_g g^{(n)}) \qquad \text{Formula (4)}$$

In this case $g^{(n)}$ is the image of the n-th iteration from which the image $g^{(n+1)}$ of the n+1-th iteration is calculated on the basis of formula (4). The iteration process is started with $g^{(0)} = f$. It can be seen that at each iteration a synchronization takes place between the measured data $R_f f$ and the projections obtained from the current image $g^{(n)}$ with the aid of a forward projection with $R_g$. The greater this deviation is, the more the next image $g^{(n+1)}$ will differ from the current image $g^{(n)}$.

The iteration equation according to formula (4) is applied to all images of the time series.

The result of the iteration is all the better, the better the polychromatic forward projection operator $R_g$. In the following it is described how a particularly suitable operator $R_g$ can be constructed.

The projection value q(L) is measured for beam L:

$$q(L) = -\ln \int dE e^{-\int dL \mu(E,r)} \qquad \text{Formula (5)}$$

where $\mu(E,r)$ is the attenuation value being sought. This is dependent on the energy E of the X-ray radiation and on the location r within the image. The attenuation value $\mu(E,r)$ can be subdivided into its energy-dependent contribution $\psi(E)$ and its spatial distribution g(r).

In the following the subject is divided into three materials:

$$\mu(E, r) = \sum_{i=1}^{3} g_i(r)\psi_i(E) = g(r) \cdot \psi(E) \qquad \text{Formula (6)}$$

where i indexes the three materials water, bone and iodine. $g_i(r)$ is therefore a part-image corresponding to a specific material. If formula (6) is inserted into formula (5), the following is obtained:

$$q = R_g g = -\ln \int dE e^{-\int dL g(r) \cdot \psi(E)} \qquad \text{Formula (7)}$$

The energy dependencies $\psi_i(E)$ are known, see FIG. 3. The spatial material distributions $g_i(r)$ must therefore be known in order to be able to determine $R_g g$. This means it must be ascertained at which pixels which of the three components is located.

The different components are distinguished by determining the changes in the pixel values over time. As already mentioned, as is usual with perfusion measurements, a series of temporally succeeding data sets of the same section through the examination subject is recorded, a first image f being calculated from each measured data set. If scans of the heart are taken, the data is acquired or, as the case may be, the images are reconstructed in such a way that all the images correspond to the same cardiac phase, e.g. the diastole. The first image belongs to the time instant $t_0$ before contrast agent is injected or has arrived in the region being studied.

There is therefore a plurality of images f(r,t), where each image belongs to a measurement time instant t. From this, a time-averaged image is calculated:

$$\langle f(r) \rangle = \frac{1}{T} \int dt f(r, t) \qquad \text{Formula (8)}$$

In this case T corresponds to the time interval within which the different measured data sets were acquired. From this, the standard deviation is calculated:

$$\sigma(r) = \sqrt{\langle (\langle f(r) \rangle - f(r, t))^2 \rangle} \qquad \text{Formula (9)}$$

With $\sigma(r)$ an image is therefore available whose individual values are the standard deviations of the individual pixels within the image series. The standard deviation indicates the changes in the pixel values within the image series. Since all the images represent the same section of the examination subject, the change in the pixel values comes about on the one hand as a result of the dynamics of the contrast agent and on the other hand as a result of a possibly present movement of the examination subject.

The contribution of the movement of the examination subject to the standard deviation is eliminated as follows: the first of the images, i.e. the image $f(r,t_0)$, is considered and the gradients are calculated within this image. This can be accomplished e.g. by application of a two-dimensional edge filter. Those pixels at which edges are located in the gradient image are set to 0, while all other pixels are set to 1. The standard deviation image $\sigma(r)$ is multiplied pixel by pixel by said modified gradient image. This corrected standard deviation image $\sigma(r)$ is considered below.

A weighting function is defined:

$$\omega(\tau) = \frac{1}{2} \begin{cases} 0 & \text{if } \tau \leq -\Delta\tau \\ 1 + \sin\left(\frac{\tau}{\Delta\tau}\frac{\pi}{2}\right) & \text{if else } \tau \leq \Delta\tau \\ 2 & \text{else} \end{cases} \qquad \text{Formula (10)}$$

The function $\omega(r)$ therefore has the value 0 for $\tau \leq -\Delta\tau$, for the value 1 for $\tau \geq \Delta\tau$, and in between it increases between 0 and 1. The variable $\Delta\tau$ determines the width of the transition region between 0 and 1.

Three limit values $\tau_1$, $\tau_2$ and $\tau_3$ are introduced in order to distinguish between the three different materials water, bone and iodine. The standard deviation image $\sigma(r)$ is also used for the differentiation, as will be explained in greater detail below; for owing to the elimination of the movement of the examination subject said image now shows only regions that change with time due to the presence of iodine.

One weighting image in each case is determined for each of the three components water, bone and iodine, where $u_{Wa} = (1-\omega(\sigma(r)-\tau_1))\cdot(1-\omega(g(r,t)-\tau_2))+\omega(\sigma(r)-\tau_1)\cdot(1-\omega(g(r,t)-\tau_3))$ is the weighting image for water, $u_{Bo} = (1-\omega(\sigma(r)-\tau_1))\cdot\omega(g(r,t)-\tau_2)$ is the weighting image for bone, $u_{Jo} = \omega(\sigma(r)-\tau_1)\cdot\omega(g(r,t)-\tau_3)$ is the weighting image for iodine.

The image for the respective material is obtained by pixel-by-pixel multiplication of a weighting image by the starting image $g(r,t)$. In other words, the water image $g_{Wa}(r,t)$ is obtained by $g(r,t)\cdot u_{Wa}$, the bone image $g_{Bo}(r,t)$ is obtained by $g(r,t)\cdot u_{Bo}$, and the iodine image $g_{Jo}(r,t)$ is obtained by $g(r,t)\cdot u_{Jo}$, where $u_{Wa}+u_{Bo}+u_{Jo}=1$ applies. In other words, the starting image $g(r,t)$ is obtained once again by addition of the part-images $g_{Wa}(r,t)$, $g_{Bo}(r,t)$ and $g_{Jo}(r,t)$.

The use of the weighting images in order to obtain the images $g_{Wa}(r,t)$, $g_{Bo}(r,t)$ and $g_{Jo}(r,t)$ is explained with reference to FIG. 4. Starting from the image $g(r,t)$, this is multiplied pixel by pixel by $\omega(\sigma(r)-\tau_1)$ (right-hand branch), and by $1-\omega(\sigma(r)-\tau_1)$ (left-hand branch).

The values of the standard deviation image $\sigma(r)$ are transformed into the range around 0 by subtracting $\tau_1$ from the standard deviation image $\sigma(r)$. If the weighting function $\omega(r)$ from formula (10) is applied to said shifted standard deviation image $\sigma(r)-\tau_1$, a mask image is obtained in which only pixels having a high standard deviation have the value 1, whereas pixels having a small standard deviation have the value 0; between these two extremes n there is a transition region having values between 0 and 1. Multiplying said mask image pixel by pixel by the image $g(r,t)$ yields the image $g_{dyn}(r,t)$, where the index dyn stands for dynamic. For in the case of this image $g_{dyn}(r,t)$, in comparison with the starting image $g(r,t)$, all pixels having a strongly time-variable value retain the value of the starting image $g(r,t)$ because they have been multiplied by 1, whereas all pixels having a weakly time-variable value have received the value 0 as a result of being multiplied by 0.

The reverse applies to the left-hand branch. In this case the starting image $g(r,t)$ is multiplied, not by the mask image $\omega(\sigma(r)-\tau_1)$, but by the reverse mask $1-\omega(\sigma(r)-\tau_1)$. In this way the image $g_{stat}(r,t)$ is obtained, where the index stat stands for static. For in the case of said image $g_{stat}(r,t)$, in comparison with the starting image $g(r,t)$, all pixels having a non-time-variable or weakly variable value retain the value of the starting image $g(r,t)$ because they have been multiplied by 1, whereas all pixels having a strongly time-variable value have received the value 0 as a result of being multiplied by 0.

In the first step described, the dynamic and static components of the starting image $g(r,t)$ have therefore been separated using the standard deviation image $\sigma(r)$ and the first threshold value $\tau_1$. In this case $g_{stat}(r,t)+g_{dyn}(r,t)=g(r,t)$ applies.

Figure 5:
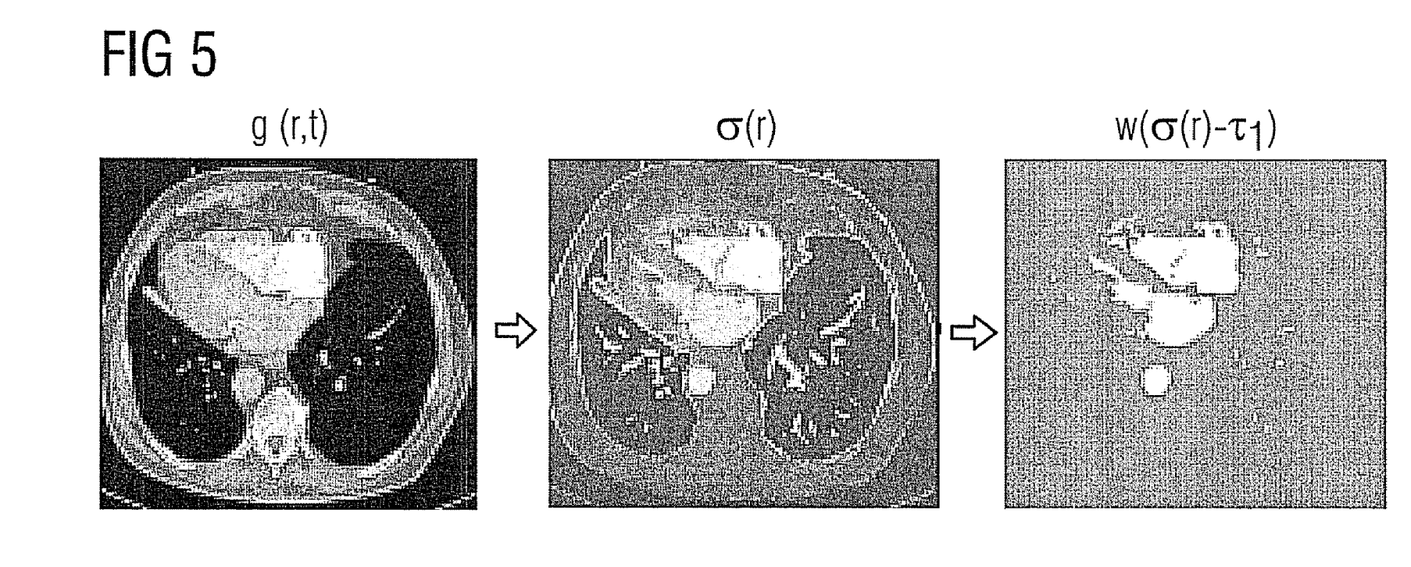
FIG. 5: shows a CT image, a standard deviation image calculated therefrom, and a modified standard deviation image.

The procedure described can be retraced and understood with reference to the CT images shown in FIG. 5. The image on the left shows the starting image $g(r,t)$. What can be seen is a section through the chest of a patient. The spinal column can be seen (bottom center), the two lungs (black area on right and left), part of the ribcage (white areas bordering the lungs), and the heart; the white dot on the left above the spinal column is the aorta. The center image is the standard deviation image $\sigma(r)$. No movement took place in the region of the spinal column. In contrast, areas of movement are: the aorta, the left atrium of the heart, and small areas within the lung and in the region of the ribs. The subsequently performed elimination of the patient movement by means of the edge detector is not shown. The right-hand image shows the application of the function $\omega(r)$ from formula (10) to the shifted standard deviation image $\sigma(r)-\tau_1$. It can clearly be seen that this image now mainly has only two CT values, the white areas corresponding to the CT value 1. These are the areas in which movement due to blood flow occurred in the course of the acquisition of the series of measured data sets.

Figure 4:
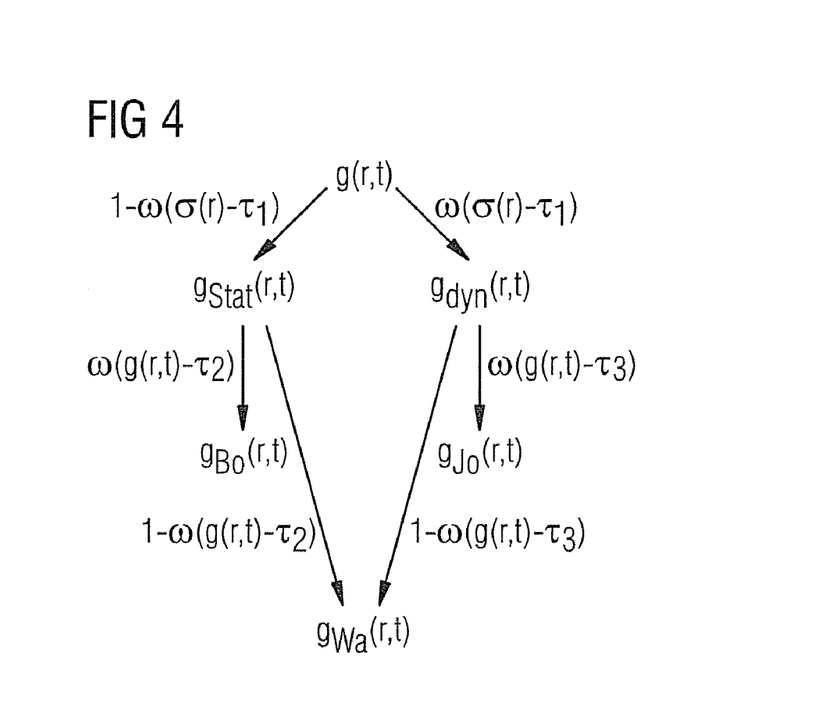
FIG. 4: shows a computational workflow for discriminating between different components of an examination subject.

The second threshold value $\tau_2$ is now inserted in the static branch of FIG. 4 in order to differentiate between bone and water. The values of the starting image $g(r,t)$ are brought into the range around 0 by subtracting $\tau_2$ from the starting image $g(r,t)$. If the weighting function $\omega(r)$ from formula (10) is applied to this shifted image $g(r,t)-\tau_2$, a mask image is obtained in which only pixels having high image values have the value 1, whereas pixels having small image values have the value 0. Multiplying this mask image pixel by pixel by the static image $g_{stat}(r,t)$ yields the image $g_{Bo}(r,t)$, where the index Bo stands for bone. For in the case of this image $g_{Bo}(r,t)$, in comparison with the static image $g_{stat}(r,t)$, all pixels having a large image value retain the value of the static image $g_{stat}(r,t)$ because they have been multiplied by 1, whereas conversely the pixels having small pixel values have received the value 0 as a result of having been multiplied by 0.

The reverse applies to the right-hand lower branch of the static branch. In this case the static image $g_{stat}(r,t)$ is multiplied, not by the mask image $\omega(g(r,t)-\tau_2)$, but by the reverse mask $1-\omega(g(r,t)-\tau_2)$. In this way a contribution to the image $g_{Wa}(r,t)$ is obtained, where the index Wa stands for water. For in the case of the water image $g_{Wa}(r,t)$, in comparison with the static image $g_{stat}(r,t)$, all pixels having a small value retain the value of the static image $g_{stat}(r,t)$ because they have been multiplied by 1, whereas all pixels having a large pixel value have received the value 0 as a result of being multiplied by 0. This is based on the fact that water has very small CT values in comparison with bone.

In the second step described, the components bone and water of the static image $g_{stat}(r,t)$ have therefore been separated using the starting image $g(r,t)$ and the second threshold value $\tau_2$.

In the dynamic branch, in contrast, the third threshold value $\tau_3$ is inserted in order to differentiate between iodine and water. The reason for differentiating water both in the static and in the dynamic branch is that there is also flowing blood present and hence dynamic components that contain no iodine. This distinction between blood containing iodine and blood that does not contain iodine can be made via the CT values of the starting image $g(r,t)$.

The values of the starting image $g(r,t)$ are transformed into the range around 0 by subtracting $\tau_3$ from the starting image $g(r,t)$, $\tau_3$ being accordingly chosen such that $\omega(g(r,t)-\tau_3)=0$ applies to regions that contain only blood without iodine, and conversely $\omega(g(r,t)-\tau_3)=1$ applies to regions that have blood containing iodine. If the weighting function $\omega(\tau)$ from formula (10) is applied to this shifted image $g(r,t)-\tau_3$, a mask image is obtained in which only pixels having high image values have the value 1, whereas pixels having small image values have the value 0; in between there is a transition region having values between 0 and 1. Multiplying this mask image pixel by pixel by the dynamic image $g_{dyn}(r,t)$ then yields the image $g_{Jo}(r,t)$, where the index Jo stands for iodine. For in the case of this image $g_{Jo}(r,t)$, in comparison with the dynamic image $g_{dyn}(r,t)$, all pixels having a large image value retain the value of the dynamic image $g_{dyn}(r,t)$ because they have been multiplied by 1, whereas all pixels having a small image value have received the value 0 as a result of being multiplied by 0.

The reverse applies to the left-hand lower branch of the dynamic branch. In this case the dynamic image $g_{dyn}(r,t)$ is multiplied, not by the mask image $\omega(g(r,t)-\tau_3)$, but by the reverse mask $1-\omega(g(r,t)-\tau_3)$. In this way a contribution to the image $g_{Wa}(r,t)$ is obtained. For in the case of the water image $g_{Wa}(r,t)$, in comparison with the dynamic image $g_{dyn}(r,t)$, all pixels having a small image value retain the value of the dynamic image $g_{dyn}(r,t)$ because they have been multiplied by 1, whereas all pixels having large image values have received the value 0 as a result of being multiplied by 0.

In the third step described, the components iodine and water of the dynamic image $g_{dyn}(r,t)$ have therefore been separated using the starting image $g(r,t)$ and the third threshold value $\tau_3$.

It is advantageous to set the parameter $\Delta\tau$ from formula (10) as a function of the currently used threshold value, not as a constant value. In this case, therefore, there exists a $\Delta\tau_1$, as well as a $\Delta\tau_2$ and a $\Delta\tau_3$, where $\Delta\tau_1$ is used when the weighting function $\omega(\ )$ is applied to an argument that contains $\tau_1$.

The three part-images $g_{Wa}(r)$, $g_{Bo}(r)$ and $g_{Jo}(r)$ are now inserted for $g_i(r)$ in formula (6) and multiplied by the respective energy-dependent attenuation profile $\psi_i(E)$. In this way $R_g g$ is obtained, see formula (7), and is inserted into the iteration equation, see formula (4). By repeated iterations an image g can now be calculated which is largely free of beam hardening artifacts. In this case the beam hardening correction was effected not simply by taking account of the CT values, which makes it impossible to differentiate iodine and bone, but also by taking into account the change over time in the CT values within the image series. This enables bone and iodine to be differentiated.

The invention has been described in the foregoing with reference to an exemplary embodiment. It is to be understood that numerous variations and modifications are possible without leaving the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of an examination subject from measured data, comprising:
acquiring a series of measured data sets during a relative rotational movement between a radiation source of a computed tomography system and the examination subject and the measured data sets relate to a same section of the examination subject at succeeding instants in time;

reconstructing first image data from each of the measured data sets, such that a series of first image data is available;

determining a change variable indicating a change over time within the series of first image data; and distinguishing between different components of the examination subject in the first image data with the aid of the change variable, the distinction being used for beam hardening correction in an iterative algorithm for calculating enhanced image data.

2. The method as claimed in claim 1, wherein the change variable specifies a change value pixel by pixel for the series of first image data.

3. The method as claimed in claim 1, wherein in the distinguishing between different components, the change variable is used to make a distinction between static components and dynamic components.

4. The method as claimed in claim 3, further comprising, distinguishing between different components within the static components, wherein the first image data is used to make a distinction between components attenuating X-ray beams to different degrees.

5. The method as claimed in claim 4, further comprising, distinguishing between different components within the dynamic components, wherein the first image data is used to make a distinction between components attenuating X-ray beams to different degrees.

6. The method as claimed in claim 3, further comprising, distinguishing between different components within the dynamic components, wherein the first image data is used to make a distinction between components attenuating X-ray beams to different degrees.

7. The method as claimed in claim 1, wherein in the distinguishing between different components, a distinction is made between any of the components: water, bone and contrast agent.

8. The method as claimed in claim 1, further comprising, determining a plurality of part-image data corresponding to the different components from the first image data.

9. The method as claimed in claim 8, further comprising, subjecting the first image data to a forward projection, when the iterative algorithm is executed, and linking each of the plurality of part-image data with an X-ray-energy-dependent attenuation variable that is specific to a respective component.

10. The method as claimed in claim 1, further comprising, correcting the change variable before the distinguishing between different components, by at least partially removing movements of the examination subject from the change variable.

11. The method as claimed in claim 1, wherein the acquiring the series of measured data sets includes acquiring a perfusion measurement.

12. The method of claim 1, wherein the reconstructing is performed on a series of more than two sets of first image data from each of the measured data sets.

13. A control and computing unit for reconstructing image data of an examination subject from measured data of a computed tomography (CT) system, said control and computing unit comprising:

a program memory device to store program code to, when executed on the control and computing unit, reconstruct first image data from each of a plurality of measured data sets, such that a series of first image data is available;

determine a change variable indicating a change over time within the series of first image data; and make a distinction between different components of the examination subject in the first image data with the aid of the change variable, the distinction being used for beam hardening correction in an iterative algorithm for calculating enhanced image data.

14. The control and computing unit of claim 13, wherein the reconstructing the first image data is performed such that a series of more than two sets of first image data is available.

15. A CT system including the control and computing unit as claimed in claim 13.

16. A non-transitory computer readable medium including program segments for, when executed on a computer device, causing the computer device to implement the method of claim 1.

17. A computed tomography, (CT) system for reconstructing image data of an examination subject from measured data, wherein a series of measured data sets is acquired during a relative rotational movement between a radiation source of a computed tomography system and the examination subject and the measured data sets relate to a same section of the examination subject at succeeding instants in time, the CT system comprising:

an image reconstruction device configured to reconstruct first image data from each of the measured data sets, such that a series of first image data is available;

a computer device configured to determine a change variable indicating a change over time within the series of first image data; and a computer device configured to make a distinction between different components of the examination subject in the first image data with the aid of the change variable, the distinction being used for beam hardening correction in an iterative algorithm for calculating enhanced image data.

18. The CT system of claim 17 wherein the series of first image data comprises more than two sets of first image data.

* * * * *